United States Patent [19]
Goldberg et al.

[11] Patent Number: 5,176,903
[45] Date of Patent: Jan. 5, 1993

[54] ANTIPERSPIRANT/DEODORANT CONTAINING MICROCAPSULES

[75] Inventors: Marvin Goldberg, Marlboro, N.J.; David M. Kellner, Hollis, N.Y.

[73] Assignee: Revlon Consumer Products Corporation, New York, N.Y.

[21] Appl. No.: 627,143

[22] Filed: Dec. 13, 1990

[51] Int. Cl.⁵ .......... A61K 7/34; A61K 7/38; A61K 9/14

[52] U.S. Cl. .......... 424/66; 424/DIG. 5; 424/67; 424/68; 424/80; 424/81; 424/401

[58] Field of Search .......... 424/65, 66, 67, 68, 424/80, 81, 450

[56] References Cited

U.S. PATENT DOCUMENTS

| | | | |
|---|---|---|---|
| 3,691,271 | 9/1972 | Charle et al. | 424/68 |
| 4,605,554 | 8/1986 | Prussin et al. | 424/68 |
| 4,639,369 | 1/1987 | Ciandelli | 424/59 |
| 4,724,240 | 2/1988 | Abrutyn | 424/59 |
| 4,818,522 | 4/1989 | Ferentchak et al. | 424/67 |
| 5,039,518 | 8/1991 | Barone et al. | 424/63 |

FOREIGN PATENT DOCUMENTS

| | | | |
|---|---|---|---|
| 2723682 | 4/1978 | Fed. Rep. of Germany | 424/81 |
| 2486396 | 1/1982 | France | 424/81 |

OTHER PUBLICATIONS

Pharmaceutical Formulas, 1946, vol. II p. 150.

Primary Examiner—Dale R. Ore
Attorney, Agent, or Firm—Julie Blackburn

[57] ABSTRACT

An antiperspirant/deodorant composition containing a cosmetically effective amount of microcapsules which encapsulate a composition comprised of fragrance and an ester.

15 Claims, No Drawings

ANTIPERSPIRANT/DEODORANT CONTAINING MICROCAPSULES

TECHNICAL FIELD

The invention is directed to an antiperspirant/deodorant composition containing microcapsules. The microcapsules encapsulate a composition comprised of fragrance oil and esters.

BACKGROUND OF THE INVENTION

Deodorants are preparations which have antimicrobial activity and which mask, remove, or decrease perspiration odor. Antiperspirants are substances which have astringent action and inhibit the flow of perspiration. Salts of metals such as aluminum, zirconium, zinc, etc. have astringent properties and are often used in antiperspirants. Most of the antiperspirant salts which show good astringency properties have a low pH (2.5 to 4.2), which in turn makes them potentially irritating to skin in susceptible individuals. Antiperspirant/deodorant manufacturers often counteract the potentially irritating effects of low PH antiperspirant salts by including soothing materials such as emollients in the formulation. However, as the user sweats the emollients are washed away in a short time thus their soothing effects do not last as long as desired.

Microencapsulation technology is well known in the art and is generally directed to encapsulating core materials that require protection until time of use in a protective covering. More recently microcapsules have been developed which are "time release". Time release microcapsules release their core materials at a controlled rate. The result is that the core material has a longer effective life since it is not immediately released from the protective microcapsule. The benefits of controlled release are obvious. For example, when pharmaceuticals are in the controlled release format, it generally allows the user to ingest or apply one long acting dose of drug instead of being obliged to ingest many small doses throughout a time period.

The encapsulation of fragrances is well known in the art. Fragrance capsules are often found in scratch and sniff inserts in magazines, in perfumes, deodorants, and a host of other applications. In the case of antiperspirants the desireability of microcapsules containing a soothing emollient is obvious. Timed release of the emollient from the microcapsule will allow its beneficial effects to have a longer effective life. This will in turn potentially counteract the irritating effects of antiperspirant salts in sensitive individuals.

SUMMARY OF THE INVENTION

The invention is directed to an antiperspirant/deodorant composition containing a cosmetically effective amount of microcapsules which encapsulate a composition comprising fragrance oil and a diester of the formula:

wherein
$R_1$ is a hydrocarbon radical having 17 carbon atoms with 0-3 double bond therein.
$R_2$ is a straight or branched chain hydrocarbon radical having 1-22 carbon atoms.
x is 0-5
y is 0-10

DETAILED DESCRIPTION

The antiperspirant/deodorant composition of the invention may be in the form of a solid stick, an aerosol, a pump spray, a roll-on, cream, lotion, or powder. In addition the composition of the invention may be a clear antiperspirant/deodorant in the solid stick, aerosol, roll-on, cream, lotion, etc. A conventional solid stick generally comprises a wax base into which the antiperspirant salts are incorporated. A suitable wax base generally comprises one or more waxes, and if desired a number of nonessential constituents such as suspending agents, whitening agents, payoff enhancers, absorbants, wetting agents, and so on. Roll-ons and lotions are liquid based with various possible liquids serving as the vehicle. Silicones, glycols, emollients, and so on represent some of the suitable vehicles. A number of nonessential constituents such as suspending agents, drying agents, emollients, etc. may be added to enhance cosmetic effects. In antiperspirant creams the vehicle is a cream. Generally creams contain oils and light waxes to provide the cream effect. It may also be desired to add nonessential but desireable constituents such as suspending agents, silicones, alcohol, whitening agents, and so forth. Antiperspirant powders are obviously powder based. The vehicle comprises powder constituents such as talc, kaolin, and other similar powder constituents. Other antiperspirant types include pads and gels.

The microcapsules of the invention may be incorporated into any of the above forms of antiperspirant/deodorant. Generally a cosmetically effective amount of microcapsules ranges from 0.01–10.0%, with 0.1–5.0% preferred, and 0.5–1.0% most preferred.

The microcapsules encapsulate a composition comprised of fragrance oil and an ester of the formula:

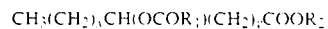

wherein
$R_1$ is a hydrocarbon radical having 17 carbon atoms with 0-3 double bond therein.
$R_2$ is a straight or branched chain hydrocarbon radical having 1-22 carbon atoms.
x is 0-5
y is 0-10

The composition encapsulated within the microcapsule can vary with respect to the proportion of fragrance or ester. For example, the microcapsule can contain from 1-99% fragrance or from 1-99% ester. Obviously the greater the concentration of the ester the greater the potentially soothing effects of the antiperspirant/deodorant containing the microcapsule.

Suitable fragrance oils vary widely and may be selected based upon preference.

Esters of the above formula which are particularly suitable are methyl oleoyl oxyvalerate, ethyl oleoyl oxyvalerate, isopropyl oleoyl oxyvalerate, butyl oleoyl oxyvalerate, isobutyl oleoyl oxyvalerate, octyl oleoyl oxyvalerate, ethylhexyl oleoyl oxyvalerate, isocetyl oleoyl oxyvalerate, isodecyl oleoyl oxyvalerate, octyldodecyl oleoyl oxyvalerate, isostearyl oleoyl oxyvalerate, amyl oleoyl oxyvalerate, methyl oleoyl oxystearate, ethyl oleoyl oxystearate, ethyl linoleoyl oxystearate, propyl oleoyl oxystearate, propyl linoleoyl oxystearate, butyl linolenoyl oxystearate, isopropyl linoleoyl oxystearate, isopropyl oleoyl oxystearate, isopropyl linolenoyl oxystearate, butyl oleoyl oxystearate, butyl linoleoyl oxystearate, isobutyl oleoyl oxystearate, isobutyl linoleoyl oxystearate, isocetyl linoleoyl stearate, isostearyl oleoyl oxystearate, isostearyl linoleoyl oxystearate, octyl linolenoyl oxystearate, isodecyl linoleoyl oxystearate, isodecyl oleoyl oxystearate, isodecyl linolenoyl oxystearate, amyl oleoyl oxystearate, amyl linoleoyl oxystearate, octyldodecyl oleoyl oxystearate, octyldodecyl linoleoyl oxystearate, etc. These compounds are set forth in U.S. Pat. Nos. 4,867,965, 4,567,037, and 4,639,369, which are hereby incorporated by reference. These esters provide beneficial emollient effects which counteract the potentially irritating effects of antiperspirant salts. Their inclusion in a microcapsule enhances their useful life, so that they are not immediately washed away by perspiration.

The microcapsules may be made by methods well known in the art. Microcapsules or encapsulates are generally made by coacervation or spray drying. The coacervation process first involves the formation of a liquid of three immiscible phases: a core material phase which comprises the materials which are to be encapsulated (in this case the fragrance oil/ester phase), a solution (generally aqueous), and a coating material phase which comprises the materials from which the microcapsule is to be made. The core material phase is emulsified in the solution and the coating material phase. The coating material phase is deposited around the droplets of core material phase and the coating is rigidized to form self-sustaining particles of a size which varies from 5 to 5000 microns. The core material may be broken out of the microcapsule by breaking the outer wall by pressure, melting, external force, decomposition, dissolving, or diffusion of the core material through the wall.

Microcapsules may also be made by the spray drying process. In spray drying, first an emulsion of the liquid core material and an aqueous solution of the coating material phase is made. The emulsion is then broken up into droplets of the desired size by spraying the emulsion from a nozzle or other similar apparatus. The moisture is removed from the droplets in a dry atmosphere such as a drying oven, and the coating material is solidified around the core material to form solid microcapsules.

The microencapsulation methods of U.S. Pat. Nos. 3,971,853, 3,091,577, 3,565,559, and Kirk-Othmer Encyclopedia of Chemical Technology, Third Edition, Vol. 15, pages 470-493 (1981) which are hereby incorporated by reference, illustrate encapsulation methods which are suitable for use with the invention. Also, encapsulation methods which are multilayer systems incorporating thousands of individual droplets of core materials such as those manufactured by Encapsulation Technologies, Inc. are suitable. The encapsulation of esters either alone or in combination with other suitable materials may occur within a water-soluble or swellable matrix, said matrix being dispersed in the continuous phase of the product. The matrix forms a barrier to the extraction of a substantial portion of the ester into the continuous phase of the product during the manufacture and shelf life of the product, matrix providing for the release of the ester upon contact with moisture periodically present in the axillary region during use of the product. Also, sponge systems which act by entrapping core materials are suitable, such as those manufactured by Dow Corning under the trademark Polytrap.

It is preferred that the coating material be starches, polysaccharides or mixtures thereof. Generally a coating material of this composition provides the most desireable time release properties when used with the antiperspirant/deodorant of the invention. Also, it is important that the coating material be of a composition that is compatible with the antiperspirant/deodorant formulation. Otherwise the microcapsule will be dissolved by the ingredients of the formulation prior to the purchase and use of the product by the consumer. Generally coating materials of a starch/polysaccharide constituency have excellent compatibility with antiperspirant/deodorant formulations. Most preferred is a coating material comprising 10-30% modified food starch, 69-90% of three or more animal or vegetable disaccharides or polysaccharides. It may be desired to add small amounts of other constituents such as flow agents, system stabilizers and so forth. The microcapsule containing the fragrance/ester is made by spray drying the emulsion and drying the droplets in drying oven. The resulting microcapsules are suitable for use with the antiperspirant/deodorant of the invention.

As mentioned previously, the spray drying or coacervation process can yield microcapsules of 5-5000 microns. Preferably the microcapsules of the invention are of a smaller diameter, namely 10-50 microns, for maximal effectiveness.

Preferably the microcapsules are incorporated into a solid or roll on type antiperspirant/deodorant. A cosmetically effective amount of the microcapsule ranges from 0.01-10%, or more preferably 0.5-1.0%. Although it is possible to add more or less of the microcapsule to the antiperspirant/deodorant formulation, it may not be practical to do so. For example, a large percentage of microcapsules provides a antiperspirant which is expensive to make and difficulties may be encountered in suspending the microcapsules.

One of the preferred embodiments is a solid stick antiperspirant comprising 0.05-5.0% microcapsules, 12-30% waxes, 10-70% silicone and 10-30% antiperspirant salts. The formulation may optionally contain one or more of a suspending agent, a whitening agent, an absorbant, a wetting agent, a preservative or mixtures thereof.

Suitable silicones include polydimethylsiloxane, phenyl dimethicone, dimethicone, cyclomethicone, hexamethylsiloxane, amodimethicone, trimethylsiloxysilicate, stearoxytrimethylsiloxysilicate, cetyl dimethicone copolyol, and so on. The silicone components provides a pleasant layer on the skin which enhances feel.

Suitable antiperspirant salts include aluminum bromohydrate, aluminum chlorohydrates, aluminum chloride, aluminum zirconium chlorohydrates, aluminum sulfates, potassium alum, or sodium aluminum chlorohydroxy lactate.

A wide variety of waxes may be used, their function to form a base or stick structure. Many sticks have a main wax component which is the basic stick former and one or more subordinate waxes which assist in maintaining stick structure. The alcohol waxes which are solids such as stearyl alcohol, myristal alcohol, cetyl alcohol, or tridecyl alcohols, serve as excellent main wax components. Other waxes and/or other ingredients such as beeswax, carnauba, ceresin, microcrystalline, lanolin, paraffin, ozokerite, lanolin alcohol, hydrogenated lanolin, candelilla, cocoa butter, petrolatum, shellac wax, hydrogenated castor oil, spermaceti, bran wax, capok wax, or bayberry wax, may be used as subordinate waxes.

In the preferred embodiment it is desireable to include one or more of a suspending agent, a whitening agent, a preservative, an absorbant, or a wetting agent.

A suspending agent aids in the suspension of the microcapsules and the antiperspirant salts in the composition as it is being poured or molded. Suitable suspending agents include silica, magnesium silicate, aluminum silicate, veegum, kaolin, clays such as quaternium 18 hectorite, etc. If a suspending agent is added, generally 0.025-10% is suggested.

A whitening agent provides a more commercially pleasant whiteness to the stick. Suitable whitening agents include such colorants as titanium dioxide, talc, mica, silicates, zinc oxide, etc. If a whitening agent is include generally 0.1-3.0% is suggested.

It may be desireable to add preservatives to the final commercial formulation to protect against degradation of the product if it happens to have a longer than usual shelf life. Suitable preservatives include those commonly used in cosmetics, such as the parabens (methyl, ethyl, propyl, butyl, etc.), imidazolidinyl urea, quaternium-15, benzyl alcohol, phenoxyethanol, to name only a few. If a preservative is added, generally 0.01-0.60% is suggested.

It may also be desired to add an absorbant to the formulation. An absorbant acts to absorb grease and oil, thereby enhancing the beneficial effects of the composition. Suitable absorbants include talc, or other powder type constituents such as mica, starch, silicates, clays, zinc oxide, aluminum hydroxide and so on. If an absorbant is added 0.5-8% is generally suggested.

A wetting agent or emulsifier is desireable. Its function is to cause the underarm sweat to easily form a contact with the antiperspirant salts which are embedded in the antiperspirant/deodorant stick. A wide variety of emulsifiers are suitable including PEG 8 distearate, PEG caprylate, PEG (5-15) Cocoate, PEG (4-150) dilaurate, PEG 2 dioctanoate, PEG (4-150) dioleate, PEG 3 dipalmitate, PEG(2-175) distearate, PEG (8-12) ditallate, PEG (6-12) distearate, glycols, and so on. The numbers in parentheses indicate the number of ethylene glycol units i.e. PEG 8 distearate is polyethylene glycol distearate with 8 ethylene glycol units. The range in parentheses indicates the range of ethylene glycol units.

One preferred embodiment of the invention where microcapsulates are incorporated into a solid antiperspirant/deodorant is an antiperspirant/deodorant comprising:
10-70% dimethicone (silicone)
0.1-3.0% titanium dioxide/talc (whitening agent)
0.025-10% silica (suspending agent)
0.5-3% talc (absorbant)
12-30% stearyl alcohol (main wax component)
0.5-4% hydrogenated castor oil (subordinate wax)
0.01-0.10 propyl paraben (preservative)
10-30% aluminum zirconium tetrachlorohydrex gly (antiperspirant salt).

A second preferred embodiment of the invention is where the microcapsules are incorporated into a roll-on antiperspirant deodorant. Roll-ons are generally liquid and comprise a vehicle into which the antiperspirant salts and other constituents are incorporated. In the preferred embodiment of the invention the roll-on comprises 10-80% silicone, 10-30% antiperspirant salts, and 0.1-5% microcapsules.

Suitable silicones and antiperspirant salts are as mentioned above.

Preferably the roll-on comprises a number of nonessential but desireable constituents such as drying enhancers, preservatives, suspending agents and so on.

A drying enhancer is a material which enables the roll on to dry more quickly. Generally an alcohol is suitable as a drying enhancer, and a $C_{1-3}$ alcohol such as isopropyl alcohol, ethanol, SD alcohol 40-B, or any SD alcohol is suitable. If the alcohol is included in the composition a range of 1-10% is suggested.

Suitable preservatives are those mentioned previously. If a preservative is included in the composition, a range of 0.0.1-0.6% is preferred.

A suspending agent aids in the suspension of the microcapsules and antiperspirant salts. Suitable suspension agents are as mentioned above. A range of 1-5% is suggested.

The preferred roll on composition comprises:
0.01-10% microcapsules
10-30% aluminum zirconium tetrachlorohydrex gly (antiperspirant salts)
10-70% cyclomethicone (silicone)
1-10% dimethicone (silicone)
1-10% SD alcohol 40-B (drying enhancer or alcohol)
1-5% silica (suspending agent)
0.001-5.0% quaternium 18 hectorite (suspending agent)

The above antiperspirant/deodorant formulations provide excellent antiperspirant activity. The presence of the microcapsules containing the specific esters provide time release of a skin soothing component which acts to counteract the harsh effects of antiperspirant salts in sensitive individuals.

The invention will be further described in connection with the following examples which are set forth for the purposes of illustration only.

EXAMPLE 1

A solid antiperspirant/deodorant was prepared as follows:

|  | w/w % |
|---|---|
| Cyclomethicone | 53.62 |
| Titanium dioxide/talc | 0.250 |
| Silica | 0.250 |
| Talc | 1.000 |
| Stearyl alcohol | 18.000 |
| Hydrogenated castor oil | 5.000 |
| PEG-8 Distearate | 0.050 |
| Propyl paraben | 0.050 |
| Aluminum zirconium tetrachlorohydrex gly | 20.000 |
| Optimax microcapsules* | 0.830 |
|  | 100.00 |

*The microcapsules were obtained from Encapsulation

The composition within the microcapsule comprised approximately 95% fragrance and 5% isopropyl linoleoyl stearate. The coating material of the microcapsule was approximately 10-30% food starch, and 69-90% of three or more animal or vegetable origin disaccharides and polysaccharides. The microcapsule was made as follows: In a suitable steam-jacketed vessel, 18 parts of polysaccharide and 2 parts disaccharide in 50 parts deionized water as dispersed. The polysaccharide content may comprise a single polysaccharide or mixture of two or more polysaccharides. The polysaccharide should possess emulsifying properties either inherently or by reason of the presence of a minor proportion of a suitable emulsifying agent. The mixture was heated to 140° F. and the components dissolved thoroughly.

Thirty parts of a mixture of suitable fragrance oil and "ester" were dispersed thoroughly, then homogenized to achieve a dispersed phase of the fragrance oil/ester with a mean droplet size of 0.5 microns or less while maintaining the mixture at 120° F. to 130° F.

While maintaining continued agitation, the resulting homogeneous mixture was fed into a suitable spray dryer with an inlet air temperature of 400° F. and an outlet air temperature of 220° F., using high speed rotary atomization, such that the resulting, dried particles had a mean particle size of appx. 20 microns and a residual moisture content of greater than or equal to 3%. The resulting powder was optionally screened to ensure a maximum particle size of greater than or equal to 100 microns.

EXAMPLE 2

A solid antiperspirant/deodorant was made as follows:

| | w/w % |
|---|---|
| Cyclomethicone | 53.12 |
| Titanium dioxide/talc | 0.250 |
| Silica | 0.250 |
| Talc | 1.000 |
| Stearyl alcohol | 18.000 |
| Hydrogenated castor oil | 5.000 |
| PEG-8 distearate | 1.000 |
| Propyl paraben | 0.050 |
| Aluminum zirconium tetrachlorohydrex gly | 20.000 |
| Fragrance | 0.500 |
| Optimax microcapsules* | 0.830 |
| | 100.00 |

*Encapsulated Technologies, Inc., Nyack, New York

EXAMPLE 3

A roll on antiperspirant/deodorant was formulated as follows:

| | w/w % |
|---|---|
| Aluminum zirconium tetrachlorohydrex gly | 20.0000 |
| Cyclomethicone | 68.1690 |
| Dimethicone | 5.0000 |
| SD alcohol 40-B | 3.0000 |
| Fragrance | 0.5000 |
| Silica | 2.5000 |
| Quaternium 18 hectorite | 0.0001 |
| Optimax microcapsules* | 0.8300 |
| | 100.0000 |

*Encapsulated Technologies, Inc., Nyack, New York

While the invention has been described in connection with the preferred embodiment, it is not intended to limit the scope of the invention to the particular form set forth, but, on the contrary, it is intended to cover such alternatives, modifications, and equivalents as may be included within the spirit and scope of the invention as defined by the appended claims.

We claim:

1. An antiperspirant/deodorant composition containing 0.01–10% microcapsules wherein the microcapsule wall comprises 1–30% food starch and 69–90% of a mixture of three or more disaccharides or polysaccharides, which microcapsule encapsulates a composition comprised of fragrance oil and an ester of the formula:

$$CH_3(CH_2)_x CH(OCOR_1)(CH_2)_y COOR_2$$

wherein $R_1$ is a hydrocarbon radical having 17 carbon atoms with 0–3 double bonds therein;

$R_2$ is a straight or branched chain hydrocarbon radical having 1–22 carbon atoms;

x is 0–5 y is 0–10

12–30% of a wax selected from the group consisting of stearyl alcohol, myristal alcohol, cetyl alcohol, tridecyl alcohol, beeswax, carnauba, ceresin, microcrystalline, lanolin, paraffin, ozokerite, lanolin alcohol, hydrogenated lanolin, candelilla, cocoa butter, petrolatum, shellac wax, hydrogenated castor oil, spermaceti, bran wax, capok wax, bayberry wax, or mixtures thereof, 10–80% silicone, and 10–30% of an antiperspirant salt selected from the group consisting of aluminum bromohydrate, aluminum chlorohydrates, aluminum chloride, aluminum zirconium chlorohydrates, aluminum sulfates, potassium alum, sodium aluminum chlorohydroxy lactate, or mixtures thereof.

2. The composition of claim 1 further comprising an ingredient selected from the group consisting of a whitening agent, a suspending agent, an oil absorbing agent selected from the group consisting of talc, mica, starch, silicates, clay, zinc oxide, aluminum hydroxide, or mixtures thereof, a wetting agent, a preservative, or mixtures thereof.

3. The composition of claim 2 comprising 0.1–3.0% whitening agent, 0.025–10% suspending agent, 0.5–3% absorbant, 0.5–5% wetting agent, 0.01–0.60% preservative or mixtures thereof.

4. The composition of claim 5 wherein the whitening agent is titanium dioxide.

5. The composition of claim 6 wherein the suspending agent is silica or Quaternium 15 Hectorite, or mixtures thereof.

6. The composition of claim 7 wherein the absorbant is talc.

7. The composition of claim 8 wherein the wetting agent is PEG 8 Distearate.

8. The composition of claim 6 wherein the preservative is propyl paraben.

9. An antiperspirant/deodorant composition comprising:

0.01–10% microcapsules wherein the microcapsule wall comprises 1–30% food starch and 69–90% of a mixture of three or more disaccharides or polysaccharides, which microcapsule encapsulates a composition comprised of fragrance oil and an ester of the formula:

$$CH_3(CH_2)_x CH(OCOR_1)(CH_2)_y COOR_2$$

wherein $R_1$ is a hydrocarbon radical having 17 carbon atoms with 0–3 double bonds therein, $R_2$ is a straight or branched chain hydrocarbon radical having 1–22 carbon atoms, x is 0–5 y is 0–10

10–80% silicone.

10–30% of an antiperspirant salt selected from the group consisting of aluminum bromohydrate, aluminum chlorohydrates, aluminum chloride, aluminum zirconium chlorohydrates, aluminum sulfates, potassium alum, sodium aluminum chlorohydroxy lactate, or mixtures thereof.

10. The composition of claim 9 further comprising an ingredient selected from the group consisting of a drying enhancer, a preservative, a suspending agent, or mixtures thereof.

11. The composition of claim 10 comprising 1-10% alcohol, 0.01-0.60% preservative, 1.0-5% suspending agent or mixtures thereof.

12. The composition of claim 11 wherein the alcohol is a $C_1$-$C_3$ organic alcohol.

13. The composition of claim 12 wherein the suspending agent is silica, clay, or quaternium 18 hectorite.

14. The composition of claim 13 comprising:
10-30% aluminum zirconium tetrachlorohydrex gly
10-80% cyclomethicone
1-10% SD alcohol 40-B
1-5% silica
0.001-5.0 quaternium 18 hectorite
0.01-5% microcapsules.

15. The composition of claim 7 comprising
10-80% silicone
0.1-3.0% titanium dioxide/talc
0.025-2% silica
0.5-3% talc
12-30% stearyl alcohol
0.5-4% hydrogenated castor oil
0.5-5% PEG 8 Distearate
0.01-0.60% propyl paraben
10-30% aluminum zirconium tetrachlorohydrex gly.

* * * * *